United States Patent
Modarres (10) Patent No.: US 7,593,767 B1
(45) Date of Patent: Sep. 22, 2009

(54) AMBULATORY SLEEPINESS AND APNEA PROPENSITY EVALUATION SYSTEM

(75) Inventor: Mohammad Modarres, Cleveland Heights, OH (US)

(73) Assignee: Cleveland Medical Devices Inc, Cleveland, OH (US)

( * ) Notice: Subject to any disclaimer, the term of this patent is extended or adjusted under 35 U.S.C. 154(b) by 14 days.

(21) Appl. No.: 11/453,709

(22) Filed: Jun. 15, 2006

(51) Int. Cl.
*A61B 5/04* (2006.01)
*A61B 5/08* (2006.01)

(52) U.S. Cl. .................. 600/544; 600/529; 600/534

(58) Field of Classification Search .......... 600/300, 600/301, 484, 529–543, 544, 545, 483
See application file for complete search history.

(56) References Cited

U.S. PATENT DOCUMENTS

| | | | |
|---|---|---|---|
| 5,047,930 A * | 9/1991 | Martens et al. | 600/301 |
| 5,299,118 A * | 3/1994 | Martens et al. | 600/509 |
| 6,171,258 B1 * | 1/2001 | Karakasoglu et al. | 600/529 |
| 6,497,658 B2 * | 12/2002 | Roizen et al. | 600/301 |
| 6,993,380 B1 * | 1/2006 | Modarres | 600/544 |
| 7,018,341 B2 * | 3/2006 | Wright et al. | 600/538 |
| 7,190,995 B2 * | 3/2007 | Chervin et al. | 600/544 |
| 2002/0185130 A1 * | 12/2002 | Wright et al. | 128/204.21 |
| 2004/0138576 A1 * | 7/2004 | Wright et al. | 600/533 |
| 2004/0254493 A1 * | 12/2004 | Chervin et al. | 600/544 |

OTHER PUBLICATIONS

Cherniack, N.S. Sleep apnea and its causes. J. Clin. Invest. 73(6): 1504-06, 1984.
Modarreszadeh, M., et al. Ventilatory stability and CO2 disturbances in wakefulness and quiet sleep. J. Appl. Physiol. 79(4): 1071-1081, 1995.
Dempsey, J.A., et al. Sleep-induced breathing instability. Sleep 19(3): 236-247, 1996.
Doghramji, K., Mitler, M.M., et al. A normative study of the maintenance of wakefulness test (MWT). Electroencephalography and Clinical Neurophysiology 103(5): 554-562, 1997.
Younes, M. Contributions of upper airway mechanics and control mechanisms to severity of obstructive apnea. Am J Respir Crit Care Med 168(6): 645-658, 2003.

* cited by examiner

*Primary Examiner*—Charles A Marmor, II
*Assistant Examiner*—Navin Natnithithadha
(74) *Attorney, Agent, or Firm*—Brian M. Kolkowski (57) ABSTRACT

The present invention relates to a method of analyzing a subject for excessive daytime sleepiness, and more particularly to a quick (short duration), quantitative method of analyzing a subject for sleep apnea. The present invention additionally relates a device for use in detecting excessive daytime sleepiness (EDS) and another device for detecting sleep apnea. One embodiment of the present invention includes a method of screening for sleep apnea comprising of measuring EEG signals from a subject to determine sleep onset time(s) over a measurement period, as well as measuring and analyzing respirations of the subject to determine variability of the subject's respiration about the sleep onset time(s). A determination about whether the subject has sleep apnea will be based in part on the variability of the subject's respirations about the sleep onset time(s).

20 Claims, 8 Drawing Sheets

AMBULATORY SLEEPINESS AND APNEA PROPENSITY EVALUATION SYSTEM

BACKGROUND OF THE INVENTION

1. Field of the Invention

The present invention relates to a method of analyzing a subject for excessive daytime sleepiness, and more particularly to a quick (short duration), quantitative method of analyzing a subject for sleep apnea. The present invention additionally relates a device for use in detecting excessive daytime sleepiness (EDS) and another device for detecting sleep apnea.

2. Technical Background

Nearly one in seven people in the United States suffer from some type of chronic sleep disorder, and only fifty percent (50%) of people are estimated to get the recommended seven (7) to eight (8) hours of sleep each night. It is further estimated that sleep deprivation and its associated medical and social costs (loss of productivity, industrial accidents, etc) exceed $150 billion dollars per year. Excessive sleepiness can deteriorate the quality of life and is a major cause of morbidity and mortality due to its role in industrial and transportation accidents. Sleepiness further has undesirable effects on motor vehicle driving, employment, higher earning and job promotion opportunities, education, recreation, and personal life. The National Traffic Safety Board estimates that annually there are 100,000 crashes involving fatigue, resulting in 71,000 injuries and 1,500 fatalities. The National Sleep Foundation has recently conducted a poll that revealed that 17% of drivers indicated they nodded off. The numbers were even higher in shift workers, with 20%-30% reporting a fatigue-related driving mishap in the past year.

Excessive daytime sleepiness (EDS) is a symptom describing an increased propensity to fall asleep, often during monotonous or sedentary activities. EDS and fatigue are different. A subject suffering from fatigue senses a physical weakness or lack of energy, and may not have an increased propensity to fall asleep at an inappropriate time. The underlying etiology of EDS generally falls into three categories: lifestyle/work schedule, primary sleep disorders, and secondary sleep disorders. Lifestyle and work schedule disorders result from the demands of our modern society. This lifestyle results in only an estimated 50% of people in the US getting the required 7-8 hours of sleep every night. Secondary sleep disorders include loss of sleep due to pain associated with chronic infections, neurological/psychiatric disorders, or alcohol/substance abuse disorders. Primary sleep disorders affect approximately 50 million Americans of all ages, and include narcolepsy, restless legs/periodic leg movement, insomnia, and most commonly, obstructive sleep apnea (OSA). OSA's prevalence in society is comparable with diabetes, asthma, and the lifetime risk of colon cancer. OSA is grossly under diagnosed; an estimated 80-90% of persons afflicted have not received a clinical diagnosis.

EDS is currently diagnosed via two general methods. The first is via subjective methods such as the Epworth and Stanford Sleepiness Scale, which generally involve questionnaires asking a series of qualitative questions regarding subjects' sleepiness during the day. With these methods, however, it is found that the patients usually underestimate their level of sleepiness or deliberately falsify their responses because of their concern regarding punitive action, or as an effort to obtain restricted stimulant medication.

The second is via physiological based evaluations such as all night polysomnography to evaluate the patients sleep architecture (e.g., obtaining a respiratory disturbance index to diagnose sleep apnea) followed by an all day test such as the Multiple Sleep Latency Test (MSLT) or its modified version, Maintenance of Wakefulness Test (MWT). The MSLT consists of four (4) to five (5) naps and is considered the most reliable objective measure of sleepiness to date. The MSLT involves monitoring the patient during twenty (20) to forty (40) minute nap periods in two-hour intervals to examine the sleep latency and the sleep stage that the patient achieves during these naps, i.e., the time it takes for the patient to fall asleep and the deepness of the sleep. A sleep disorder such as narcolepsy, for example, is diagnosed when the patient has a restful night sleep the night before but undergoes rapid eye movement sleep (REM sleep) within five (5) minutes of the MSLT naps. The MWT is a variation of the MSLT. The MWT provides an objective measure of the ability of an individual to stay awake. The MWT is an all-day test of wakefulness that is performed under identical conditions to MSLT, but where the latency of sleep is determined after the patients are instructed to attempt to remain awake.

While the MSLT and MWT are more objective and therefore don't have the same limitations as mentioned for the subjective tests, the MSLT and MWT have their own limitations. Both the MSLT and MWT require an all-day stay at a specialized sleep clinic and involve monitoring a number of nap opportunities at two hour intervals throughout the day. In addition, both tests are more demanding than the overnight polysomnogram because the technician must monitor the naps and determine the sleep onset in real-time. Further, MSLT is usually not performed in OSA patients because the test is mostly prescribed for non-respiratory sleep disorders, since the mean sleep latency results from MSLT are not linearly correlated with sleepiness. Finally, studies have shown that the MSLT is not particularly suited for gauging the effects of therapeutic intervention. This was demonstrated in studies by Thorpy in 1992 and Van den Hoed et al. in 1981 showing no reliable reduction in sleepiness in patients given stimulant medications for narcolepsy.

The MWT was developed in 1982, in part, to address some of the short-comings of the MSLT method. The MWT, however, created another problem, the "ceiling effect." This is the tendency of less "sleepy" individuals to perform the MWT without falling asleep. In fact, the length of the MWT trial was lengthened from twenty (20) to forty (40) minutes in 1984 because it was observed that patients with histories of excessive daytime sleepiness were too often able to maintain wakefulness for the twenty (20) minutes. In addition, while the MSLT and MWT are objective and "broadly" quantitative tests in that they both require the patient to fall asleep during the test and they measure the number of sleep incidents during the testing regiment, these tests are too costly and lack the degree of quantitative resolution necessary to easily permit measurement of effects of therapeutic intervention and degrees.

Despite the enormity of the problem, the current methods of assessing sleepiness are limited in their utility and accuracy, as indicated in the recent research plan and recommendations of the US National Center on Sleep Disorders Research. Currently, there are a number of subjective assessments (self-reports) including Stanford Sleepiness Scale, Epworth Sleepiness Scale, etc. However, the accuracy and reliability of these questioners are limited because people usually underestimate their level of sleepiness or they deliberately falsify their responses (e.g., to avoid punitive actions). On the other hand, the only physiologically-based (EEG and other biosignals) objective and clinically validated test of sleepiness, multiple sleep latency test (MSLT), is very expensive and time consuming (requires an all-day stay in a specialized sleep clinic) and is mostly utilized for diagnosis of narcolepsy. Other objective tests are mainly behavioral (i.e., no EEG measurement) and measure sleepiness based on accuracy and speed of the subject's response to a series of visual cues (e.g., psychomotor vigilance test, PVT).

In addition, OSA is a serious problem that affects up to 4% of the male population and perhaps up to 90% of OSA patients have not yet received a clinical diagnosis. What is needed is a test to screen for excessive daytime sleepiness and more particularly for sleep apnea. This test, unlike MSLT/MWT, should be quick, cheap, broad in its utilization, and convenient (MSLT/MWT is costly, does not routinely evaluate patients with sleep-disordered breathing, and is limited to specialized sleep labs). It is therefore an object of the present invention to develop a test which screens subjects for EDS. It is further an object of the present invention to screen subjects for sleep apnea. It is still further an object of the present invention to screen subjects for OSA. It is still further an object of the present invention to develop a test, which is of short duration. It is even still another object of the present invention to develop a test that is inexpensive. It is even still another object of the present invention to develop a test which is easily portable. It is even still another object of the present invention to evaluate patients with sleep-disordered breathing.

SUMMARY OF THE INVENTION

The present invention relates to a method of analyzing a subject for excessive daytime sleepiness (EDS) as well as a quick quantitative method for analyzing a subject for sleep apnea. The present invention additionally relates a device for use in detecting EDS and another device for use in detecting subjects at high-risk for such pronounced respiratory disturbances as obstructive sleep apnea (OSA).

There are numerous embodiments of the present invention, a few of which are listed below. The invention relates to a method for analyzing a subject, preferably a human subject, for EDS and/or sleep apnea, more particularly OSA. The present invention also relates to a device for analyzing a subject, preferably a human subject, for sleep apnea and/or EDS.

Simplicity of the present methods and equipment gives this invention the advantages of time, cost, and convenience over other methods of diagnosing EDS and sleep apnea. The methods in the present invention are preferably of short duration. With fewer man-hours needed than currently used procedures, the present invention represents a major cost savings for both patients and insurance companies and a major time savings for both patient and physician. The methods described can be performed in most settings, and are not confined to a hospital or specialized sleep lab, provided there is a quiet room with a comfortable recliner chair, sofa, or bed. This means that this system could be used in a physician's office, a school nurse office, small clinics within a factory or workplace, or directly at the patient's home by the physician or trained technician. Since up to 90% of all OSA patients have not received clinical diagnosis, the portability of the device could allow it to be used in these various places to objectively screen for the presence of OSA rather than the typical method of relying on subjective self-assessment. The present invention has the potential to prioritize patients who are in needed to undergo a full PSG evaluation as soon as possible when there is a shortage of sleep lab facilities. Finally, current popular methods of clinical assessment of EDS are limited in their utilization, as patients with sleep-disordered breathing are not routinely evaluated by these tests.

In one embodiment, the present invention includes a method of screening for sleep apnea comprising of measuring EEG signals from a subject to determine sleep onset time(s) over a measurement period, as well as measuring and analyzing respirations of the subject to determine variability of the subject's respiration about the sleep onset time(s). A determination about whether the subject has sleep apnea will be based in part on the variability of the subject's respirations about the sleep onset time(s).

In another embodiment, the present invention includes a device for detecting sleep apnea comprising of at least one sensor having a first signal for measuring a subject's EEG, as well as at least one sensor having a second signal for measuring the subject's respiration rate. In addition, the present invention comprises of a processor having an input (to receive the first and second signal from the subject) and an output. The first and second signals are analyzed by the processor to make a determination based in part on the first and second signals as to whether the subject has sleep apnea and the determination is output from the processor.

In still another embodiment, the present invention includes a method of screening for EDS comprising the steps of measuring EEG signals from a subject to determine sleep onset time(s) over a measurement period. A separate test conducted at a separate time will measure the subject's response to one or more types of stimulus over measurement period. The measurements from these two tests will be used in part to determine whether the subject has EDS.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DESCRIPTION OF THE PREFERRED EMBODIMENTS

The present invention relates to a method of analyzing a subject for excessive daytime sleepiness (EDS) as well as a quick quantitative method for analyzing a subject for sleep apnea. The present invention additionally relates a device for use in detecting EDS and another device for use in detecting subjects likely to have pronounced respiratory disorders, such as hypopneas and obstructive and central sleep apneas.

Functionally, the present invention may consist of two subsystems. The first subsystem includes methods and devices automatically and objectively quantifying an individual's level of alertness based during simultaneous analysis of behavioral and neurophysiological (particularly EEG) responses from a short test which stimulates the subjects senses. A sleepy or drowsy subject will exhibit an increased response time and performance errors as well as a more sleepy EEG profile. This subsystem produces what the applicants call an alertness index, which is a quantification of the subject's overall alertness. The second subsystem includes methods and devices designed to automatically analyze the neurophysiological (particularly EEG) and respiratory related data during a short daytime nap. For this subsystem, an EEG-based profile which establishes the first stages of falling asleep is analyzed to produce what the applicants call a sleep index. This, along with the alertness index, produces an overall index relating to excessive daytime sleepiness (EDS). This index is called the index of excessive daytime sleepiness. Another test in this subsystem involves measuring the magnitude and changes in respiratory variability around the sleep onset time. This produces a novel apnea propensity index (API) which is used to predict the likelihood a subject will be afflicted with pronounced respiratory disturbances (hypopneas, obstructive and central apnea) during sleep. The API can be used as a screening tool before individuals are placed in an all-night polysomnography (PGS) study, or possibly even to diagnose sleep apnea.

Various embodiments of the present invention include a step for measuring a subject's response to one or more types of stimulus over a measurement period (the first subsystem). This step can be performed or accomplished a number of ways. Preferably, if this step is included into the method, the subject is instructed to respond to certain types of the one or more stimulus. Still further preferably, the subject's response and lack of response are measured along with the timing of the subject's response relative to the stimulus. The stimulus provided to the subject can be based on any of the subject's senses including hearing, sight, smell, touch, or taste. Preferably, because the subject may be requested to close their eyes during the test (and given the types of stimuli devices currently readily available) the stimulus is based on the subject's sense of hearing or touch. More preferably, the stimulus is based on the subject's sense of hearing. In one particular embodiment of the subject's sensory response, a processor, such as a PC computer with specialized software, is used to generate a series of auditory tones for the subject. These auditory tones are further linked to the brain wave or EEG signals of the subject. With respect to the auditory tones, the subject could be instructed to listen for a particular tone (and respond in some way) and ignore the other tones. An example of this would be to generate a series of auditory tones in the form of phonemes such as "BA" or "GI". The volume level would be set low enough such that the subject would be able to comfortably hear the tone but not too loud to disturb or startle. These tones can be communicated to the subject either through ear phones or speakers. These tones would be generated by a program or software on a computer or processor respectively. For the duration of the test, the subjects would be instructed to listen for a particular tone and ignore other tones. Preferably, the tones are at least 1.5 seconds apart. In the preferred protocol, the subject will have to press a switch (e.g., a push-button) as soon as they hear a particular tone (e.g., BA) and ignore other types of tones (GI). For embodiments of the present invention, where the protocols involve pressing a push-button or other types of switches, preferably the subject practices a few times before the start of the test to become familiar with the feel and the handling of the switch. If the subject is unable or unwilling to press the switch, protocols can be used that do not require such a manual response.

During the test, the subject's response to the stimulus is preferably measured and the accuracy of the subject's response is evaluated preferably by a computer or processor by examining the status of the subject's response (through, for example, the switch identified in the one embodiment) following the onset of the stimulus (for example, the auditory tones in the same embodiment). In the particular embodiment referred to the processor or computer would compute the time delay between the occurrence of the auditory stimulus and the time in which the switch is activated. If the subject manages to press the switch within the allowable interval immediately after the appropriate auditory stimulus (i.e., the tone for which the subject is instructed to respond), the analysis through the processor or computer assigns a correct response for that duration of the test. If, however, on the other hand the subject fails to respond or activates the switch when the stimulus was supposed to be ignored, the processor or computer assigns an incorrect response for that duration of the test. Preferably, the subject's reaction time and/or accuracy of response are used along with the analysis of the subject's brain waves (together, producing the alertness index) to help make a determination of whether the subject is suffering from EDS. Furthermore, the subject's measured response can be used as an indicator as to whether the subject is cooperating with the test by comparing the measured response with the analyzed brain wave signals over the same time period.

The therapy devices worn by the subjects or the different systems of the various embodiments of the present inventions are preferably portable. By portable it is meant among other things that the device is capable of being transported relatively easily. Relative ease in transport means that the device is easily worn and carried, generally in a carrying case to the point of use or application and then worn by the subject without significantly affecting their range of motion. Furthermore, the portable therapy device preferably should be relatively light-weight. By relatively light-weight, preferably the device weighs less than about 10 lbs., more preferably less than about 7.5 lbs., even more preferably less than about 5 lbs., and most preferably less than about 2.5 lbs. By being lightweight and compact, the device should gain greater acceptance for use by the subject. The entire therapy system including the device and other components including any processors, computers, video screens and the like preferably weigh less in total than about 20 lbs., more preferably less than about 15 lbs., and most preferably less than about 10 lbs.

This system preferably can fit in a reasonably sized carrying case so the patient or their caregiver can easily transport the system.

Figure 1:
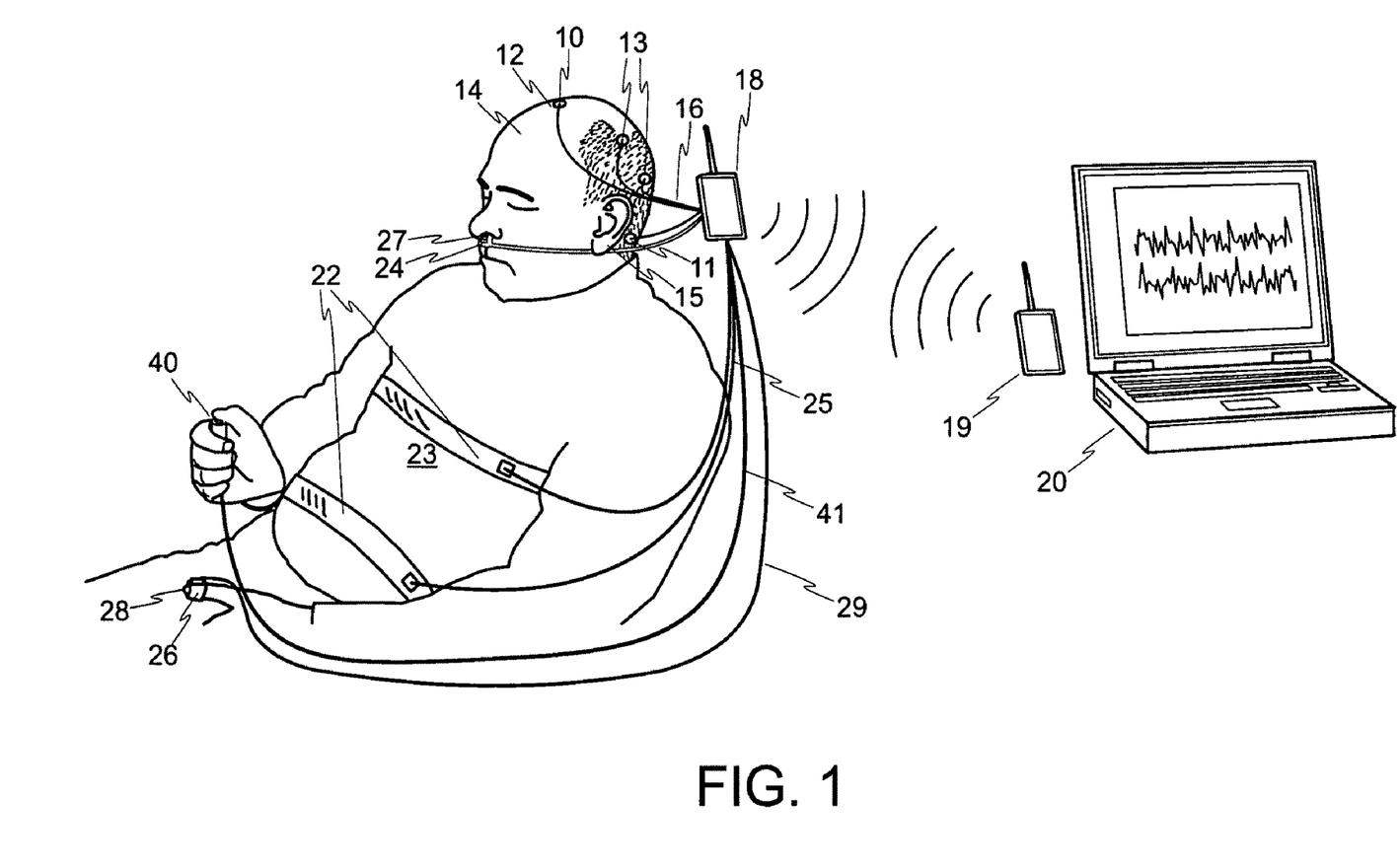
FIG. 1. is an illustration of a subject wearing a sensor to pickup and transmit brain wave signals to a computer for quantitatively analyzing the subject for excessive daytime sleepiness and/or sleep apnea.

FIG. 1 is an illustration of a subject wearing a sensor to pick up and transmit brain wave signals to a computer for quantitatively analyzing the subject for WDS and/or sleep apnea. In FIG. 1, an electrode (sensor) 10 is placed on the central lobe 12 of the subject's scalp 14, and another reference electrode (sensor) 11 is placed behind the subject's ear 15. Preferably the electrodes 10, 11, 13 are dry electrodes. The electrodes 10, 11, 13 are releasably connected to leads 16 which can be connected to a processing unit (not shown) or to a wireless telemetry unit 18, which transmits the raw brain wave or EEG signal to a receiver 19 and then processing unit 20 for analysis. It should be clear to someone skilled in the art where the placement of the electrode 10 will be required in order to maintain a close proximity between the electrode 10 and that portion of the brain from where a signal is to be recorded. The number of electrodes 10, 13 and likewise signals to be analyzed depends on the environment in which the sleep analysis system is to be used. In a more formal setting, it may be desirable to collect and analyze multiple brain wave or EEG signals from several locations on a patient's scalp. In a less formal setting such as a family practitioner's, internist's or general practitioner's office, it may be desirable to apply two sensors that require little or no expertise in placement of the electrode, i.e., a dry electrode. The electrodes can preferably be placed in the locations of the frontal (F), parietal (P), anterior (A), central (C) and occipital (O) lobes of the brain.

Referring again to FIG. 1, which is an illustration of a subject holding push-button device 40. The push-button device 40 is releasably connected to leads 41 which can be connected to a processing unit (not shown) or to a wireless telemetry unit 18, which transmits the raw behavioral response to a receiver 19 and the processing unit 20 for analysis. Also, not shown, it is clear to someone skilled in the art where the placement of the push-button device 40 will be required in order for the subject to adequately respond to external stimuli by depressing the push-button device, preferably with a finger, and most preferably with his/her thumb.

Once the sensor(s) 10 as shown in FIG. 1 are in place relative to the subject's head in order to detect a brain wave or EEG signal, the subject is preferably instructed to sit in a comfortable chair or lie down in a supine position. Further preferably, the subject is instructed to close their eyes throughout the test and relax, but to try and not fall asleep. The subject's brain wave or EEG signals are preferably recorded and analyzed during a test time period. The test time period is defined as the period of time in which the subject's brain waves signals are measured or recorded, and in general this corresponds closely to the time period in which the subject is hooked up to the quantitative, EDS measuring system. Generally, the test time period is preferably less than about 2 hours, still more preferably less than about 60 minutes, still more preferably less than about 30 minutes, even still more preferably less than about 20 minutes, even still more preferably less than 15 minutes, and most preferably less than about 10 minutes. It has been found, generally, that a given amount of test time is necessary for a subject's brain wave signals to evolve into a consistent pattern. Therefore, the period of time in which brain waves are used for analysis preferably begins after this initial period of inconsistent data and is called the measurement time period. Preferably, the measurement time period (also known as the time period over which the data is analyzed) begins at least 2 minutes after the test time period began, more preferably 4 minutes after the test time period began and most preferably 6 minutes after the test time period began. The measurement time period ends before or at the time the test time period ends.

Various embodiments of the present invention include steps for measuring and analyzing EEG signals from a subject to determine a sleep onset time(s) over a measurement period (the second subsystem). This step can be performed or accomplished a number of ways. In the simplest form, the subject can be hooked up to a sensor to measure the subject's EEG signals.

EEG signals help to determine a subject's sleep onset time. An EEG reading can indicate that the subject is awake or give a drowsy/sleep profile. An EEG-based falling asleep profile, indicating the latency of entering first stages of sleep and the average depth obtained afterwards, will automatically be processed using novel algorithms to produce a sleep index.

The present invention involves the step of using at least one sensor to measure a subject's brain wave signals over a measurement. The brain wave or EEG signals can be obtained by any method known in the art, or subsequently developed by those skilled in the art to detect these types of signals. Sensors include but are not limited to electrodes or magnetic sensors. Since brain wave signals are, in general, electrical currents which produce associated magnetic fields, the present invention further anticipates methods of sensing those magnetic fields to acquire brain wave signals similar to those which can be obtained through, for example, an electrode applied to the subject's scalp. The subject(s) referred to in the present invention can be any form of animal. Preferably the subject(s) are mammal, and most preferably human.

If electrodes are used to pick up the brain wave signals, these electrodes may be placed at one or several locations on the subject(s)' scalp or body. The electrode(s) can be placed at various locations on the subject(s) scalp in order to detect EEG or brain wave signals. Preferably for the present invention at least one electrode is placed in the occipital position. In order to obtain a good EEG or brain wave signal it is desirable to have low impedances for the electrodes. Typical EEG electrodes connections may have impedance in the range of 5 to 10 K ohms. It is in general desirable to reduce such impedance levels to below 2 K ohms. Therefore, a conductive paste or gel may be applied to the electrode to create a connection with impedance below 2 K ohms. Alternatively, the subject(s) skin may be mechanically abraded, the electrode may be amplified or a dry electrode may be used. Dry physiological recording electrodes of the type described in U.S. patent application Ser. No. 09/949,055 are herein incorporated by reference. Dry electrodes provide the advantage that there is no gel to dry out, no skin to abrade or clean, and that the electrode can be applied in hairy areas such as the scalp. Additionally if electrodes are used as the sensor(s), preferably at least two electrodes are used—one signal electrode and one reference electrode; and if further EEG or brain wave signal channels are desired the number of electrodes required will depend on whether separate reference electrodes or a single reference electrode is used. For the various embodiments of the present invention, preferably an electrode is used and the placement of at least one of the electrodes is at or near the occipital lobe of the subject's scalp.

Determination of the respiratory variability index is important in measuring sleep apnea risk levels. Development of the respiratory variability index is dependent on the analysis of respiratory flow and the EEG obtained during the nap and uses the steps that were described for EDS on the previous page. Preferably, one of features of the respiratory variability index is the dynamic variability of respiratory related signals from the devices and methods mentioned earlier about the time of sleep onset. Thus, development of the respiratory variability is based on the analysis of the subject's respirations or other factors directly or indirectly related to the respirations around the time when the EEG based sleep index approaches the sleep threshold.

Sleep onset times can be determined by monitoring a subject's respiratory patterns, based on the hypothesis that patients with OSA will manifest their first signs of respiratory variability around the time of sleep onset. These respiratory disturbances can be in the form of exaggerated variability (compared with normal patients) in milder cases of OSA, or more pronounced respiratory disturbances in more severe OSA patients. These more severe disturbances may include formal hypopneas or central/obstructive apneas.

Various embodiments of the present invention include a step for measuring and analyzing respirations directly or indirectly of a subject to determine the variability of the subject's respiration about the sleep onset time(s). This step can be performed or accomplished in a number of different ways using a variety of sensors or devices. The subject's respirations can be measured by measurement of airflow, measurement of respiratory effort, measurement of oxygenation and ventilation, and the like to the subject. Measurement of airflow is preferably measuring using sensors or devices such as a pneumotachometer, strain gauges, thermal sensors, transducers, piezo sensors, magnetometers, pressure sensors, static charge-sensitive beds, and the like. These sensors or devices, also preferably measure nasal pressure, respiratory inductance plethysmography, thoracic impedance, expired carbon dioxide, tracheal sound and the like. Measurement of respiratory effort is preferably measured by esophageal pressure, surface diaphragmatic EMG, and the like. Measurement of oxygenation and ventilation is preferably measured by pulse oximetry, transcutaneous oxygen monitoring, transcutaneous carbon dioxide monitoring, expired end carbon dioxide monitoring, and the like.

One example of such a sensor for measuring respirations either directly or indirectly is a respiration belt. Respiration belts can be used to measure a subject's abdominal and/or thoracic expansion over a measurement time period. The respiration belts may contain a strain gauge, a pressure transducer or other sensors, which can indirectly measure a subject's respirations and the variability of respirations by providing a signal which correlates to the thoracic/abdominal expansion/contractions of the subject's abdominal cavity. Respiration belts may be placed at one or several locations on the subject's torso or in any other manner know to those skilled in the art. Preferably, the respiration belts are positioned below the axilla and/or at the level of the umbilicus in order to measure rib cage and abdominal excursions. More preferably, if respiration belts are used then at least two belts are used one being positioned at the axilla and the other at the umbilicus.

Another example of such a sensor or method for measuring respirations either directly or indirectly is a nasal cannula or a facemask. The nasal cannula or facemask can be used to measure the subject's respiratory airflow. Nasal or oral airflow can be measured quantitatively and directly with a pneumotachograph consisting of a standard oxygen nasal cannula or facemask respectively connected to a pressure transducer and placed in the nares or over the subject's mouth and nose respectively. Airflow can be estimated by measuring nasal or oral airway pressure that decreases during inspiration and increases during expiration. Inspiration and expiration produce fluctuations on the pressure transducer's signal that is proportional to airflow. A modified nasal cannula or facemask may also be used which is connected to a carbon dioxide or oxygen sensor to measure respective concentrations of these gases. In addition a variety of other sensors can be connected with either a nasal cannula or facemask to either directly or indirectly measure a subject's respirations.

Still another example of such a sensor or method of either directly or indirectly measuring respirations of the subject is the use of a pulse oximeter. The pulse oximeter can measure the oxygenation of the subject's blood by producing a source of light originating from the oximeter at two wavelengths (650 nm and 805 nm). The light is partly absorbed by haemoglobin, by amounts which differ depending on whether it is saturated or desaturated with oxygen. By calculating the absorption at the two wavelengths the proportion of hemoglobin which is oxygenated can be estimated. Preferably, pulse oximeters are placed on a subject's earlobe or fingertip. More preferably, the pulse oximeter is placed on the subject's index finger.

Again referring to FIG. 1, an illustration is shown of a subject wearing respiratory effort belts, which pickup and transmit thoracic/abdominal signals to a computer for quantitatively analyzing the subject for sleep apnea. FIG. 1 also is an illustration of a subject wearing oral/nasal cannulas, which pickup and transmit oral/nasal airflow signals to a computer for quantitatively analyzing the subject for sleep apnea. FIG. 1 is further an illustration of a subject wearing a pulse oximeter, which picks up and transmits the subject's blood-oxygen levels to a computer for quantitatively analyzing the subject for sleep apnea. In FIG. 1 respiratory effort belts 22 are placed on the subjects' thoracic cavity 23. The belts 22 are releasably connected to leads 25 which can be connected to a processing unit (not shown) or to a wireless telemetry unit 18, which transmits the raw thoracic/abdominal effort signals to a receiver 19 and then processing unit 20 for analysis. It should be clear to someone skilled in the art where the placement of the belts 22 will be required in order to adequately measure expansion and contraction of the abdominal and thoracic cavities.

In FIG. 1 nasal cannulas 24 are placed in the subject's nasal cavities 27. The nasal cannulas 24 are releasably connected to a processing unit (not shown) or to a wireless telemetry unit 18, which transmits the raw oral/nasal airflow signals to a receiver 19 and then processing unit 20 for analysis. Not shown, it is clear to someone skilled in the art where the placement of the cannulas 24 will be required in order to adequately measure the influx and efflux of the patients breathing.

In FIG. 1 pulse oximeter 26 is placed on the subject's index finger 28. The pulse oximeter 26 are releasably connected to leads 29 which can be connected to a processing unit (not shown) or to a wireless telemetry unit 18, which transmits the raw pulse and oxygen signals to a receiver 19 and then processing unit 20 for analysis.

Figure 2:
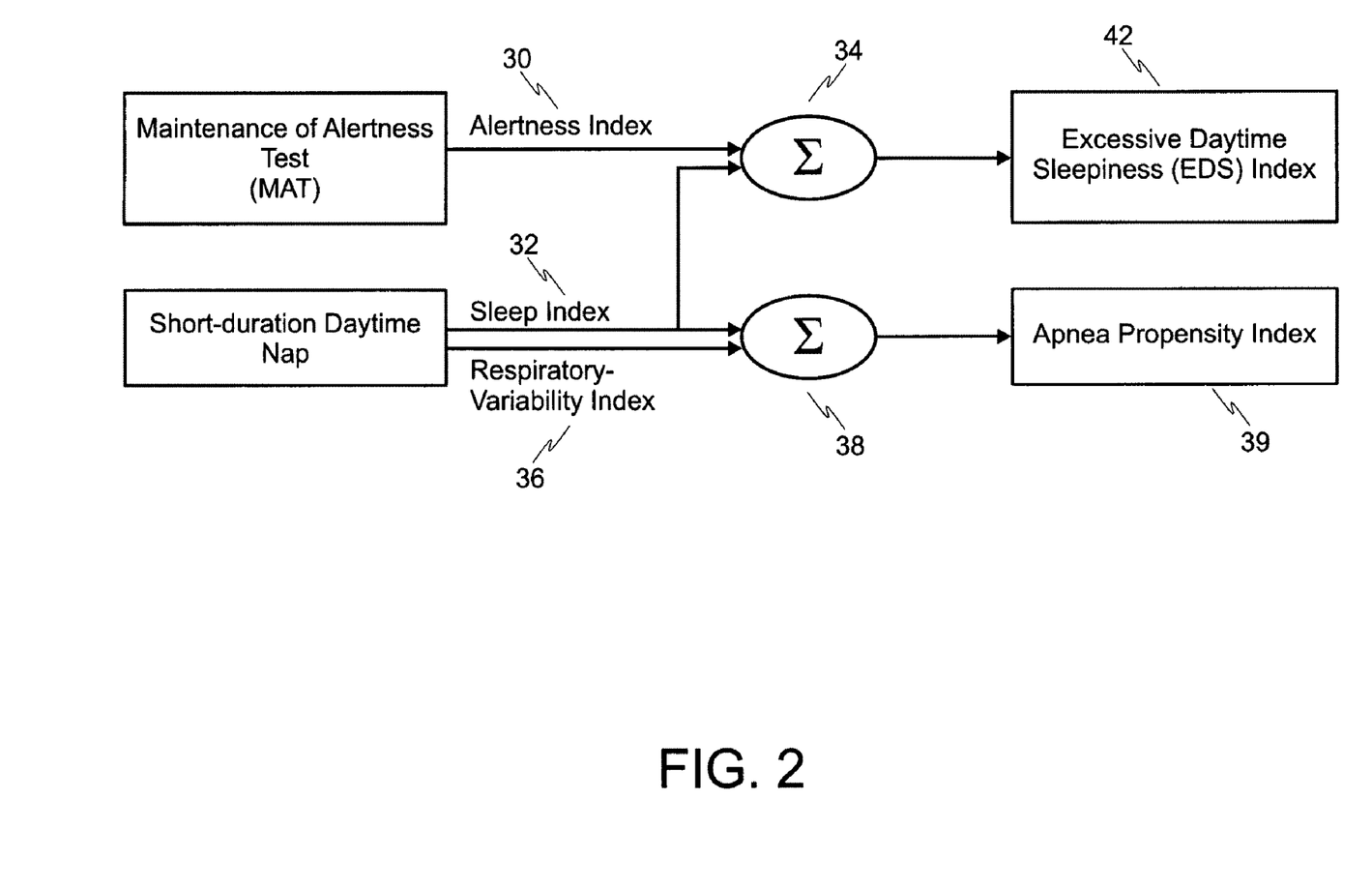
FIG. 2. is a flow diagram showing two embodiments of the test methods of the present invention.

FIG. 2 is a flow-chart showing the quantitatively calculated alertness index 30 and the quantitatively calculated sleep index 32. The sleep index 32 and alertness index 30 are quantitatively combined to calculate 34 the excessive daytime sleepiness (EDS) index 42. FIG. 2, also shows combining the sleep index 32 and respiratory-variability index 36 to quantitatively calculate 38 the apnea propensity index 39.

Figure 3:
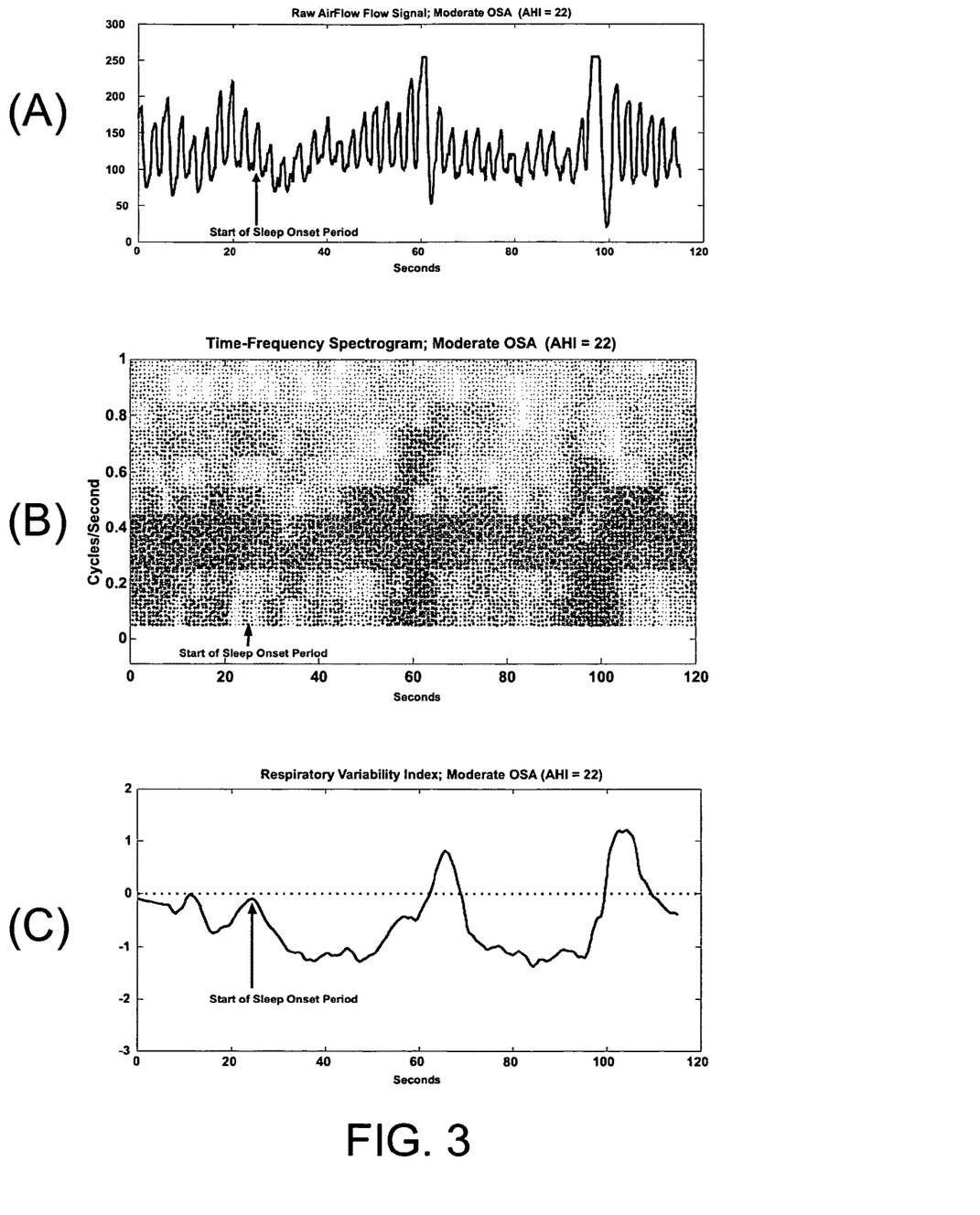
FIG. 3. is a graph showing an analog signal of the awake to sleep transition showing the scoring of a subject using the method of the present invention as well as that by a PSG technician during a MSLT.

FIG. 3 shows the step from various embodiments of the present invention of analyzing a flow signal from a subject with moderate OSA to compute the API. From top to bottom, the FIG. 3 plot A) depicts the ray air flow signal around the time that the subject entered the sleep onset period. From this air flow signal, a time frequency spectrogram is computed that displays the power spectrum of the air flow signal at each instant of time. The spectrogram of FIG. 3. B) is presented in an "image" format where the intensity of the power of the slow signal at each frequency band (cycles/second) at each instance of time is shown in various shades of gray. Thus, darker shades are indicative of more intense power in the fluctuations of the flow and lighter shades indicates relative stability. From this image, for example, it appears that most of the power is diminished in the frequencies faster than 0.5 cycles/second which corresponds to the variations of the slow signal with a period of 2 seconds (1/0.5) or less.

FIG. 3 C) shows the respiratory variability of the subject, derived from the spectrogram plot, as follows: If the power spectra density of the flow signal at time n in the frequency band of interest (0.1 to 1 cycles/second) as the $PF_n$ then the respiratory variability index at time n is defined as:

respiratory variability index $(n)=f[b1*Pf_n(0.1)^{a1}+ b2*Pf_n(0.2)^{a2}+ \ldots +b10*Pf_n(1.0)^{a10}]$ where Pfn(0.1) is the component of the power density of the flow signal in the 0 to 0.1 cycles/second at time n, etc. These power densities at each band are selectively weighted by (a1, a2, ..., a10) and (b1, b2, ..., b10) coefficients that enhance or decrease the contribution of power density at each frequency band to the overall respiratory variability index. $f$ can be a linear or non-linear function.

In one preferred embodiment, coefficients a1, a2, ..., a10 are all set to 1. Then the frequency x (x=0.1, 0.2, ..., 1.0) that has the largest power, $Pf_n(x)$, is identified and the corresponding b coefficient is set to one whereas other b coefficients are set to 0. For example, if the largest power is at frequency 0.3 (i.e., $Pf_n(0.3)$ has the maximum value), then the b coefficient corresponding to this frequency (b3) is set to 1 and all the other b's (b1, b2, b4, ..., b10) are set to zero. In this embodiment the function f is a linear filter such as a tenth order moving average filter. In another preferred embodiment, all of the coefficients a and b are set to one (1) and f is a moving average filter.

Finally, FIG. 3 C) shows that the respiratory variability index is "reduced" to a single quantity that can be defined as one embodiment of the apnea propensity index (API). A preliminary definition of API is as follows:

API=g(Resp_Var_Index ($[t_{sop}-x\text{Sec} \rightarrow t_{sop}+x\text{Sec}]$))

In further defining the API above, "$t_{sop}$" is an abbreviation for the start of sleep onset period. This quantity can correspond to the wake-sleep transition used in the standard clinical polysonmography. The preferred method for determining $t_{sop}$ is the time of the first crossing of the sleep threshold by the EEG based sleep index. Preferably, $t_{sop}$ is usually before the clinical sleep onset time which was defined previously as the start of the time when the sleep index stays above the threshold for a minimum of 90 seconds (i.e., when sleep is maintained). Thus, API is defined as a linear or non-linear function (g) of the respiratory variability index in a period of about 2x seconds where for x=120 seconds, the period correspond to 240 seconds (4 minutes around $t_{sop}$. More preferably the analysis period is for x=60 corresponding to 60 seconds before and 60 seconds after $t_{sop}$. The preferred shape of function g is the squared root of the coefficient of variation of API where the coefficient of variation is defined as the standard deviation divided by the mean:

API=[Standard deviation(Res_Var_Index($[t_{sop}-x\text{Sec} \rightarrow t_{sop}+x\text{Sec}]$)./Mean(Resp_Var_Index($[t_{sop}-x\text{Sec} \rightarrow t_{sop}+x\text{Sec}]$))$]^p$ where x=60 and p=0.5

As more data becomes available, the value of p might change based on the statistical analysis relating API to the overnight apnea hypopnea index obtained from standard clinical polysomnography.

During the testing of a subject for excessive daytime sleepiness or for sleep apnea, preferably, the subject's brain wave or EEG signals are collected and analyzed. The data analysis can be done as follows to estimate or determine a number or power spectrum profile for each sampling moment or time segment. The signals can be collected through conventional recorders, analog signal processors or similar other devices and analyze after collection, however, given the easy access to digital technology such as processors and computers preferably the collection and analysis of the brain wave or EEG signals is carried out nearly concurrently (or simultaneously) using these digital means. In one embodiment of the present invention, a processor or computer receives digitized signals based on analog signals from the sensor used to measure the subject's brain wave or EEG signals. The sampled brain wave or EEG signals are then band-pass filtered in preferably the 0.1 Hz to 50 Hz range using a digital filter, e.g. a butterworth filter. This is followed by a first step of artifact detection and removal.

In the first step of analysis after data collection, the artifacts in the data are preferably identified and removed. In artifact detection and removal, the band-pass filtered data of the brain wave or EEG sample is compared with the standard deviation of the brain wave or EEG sample over the entire test or a portion of the test in which that sample is taken. If the brain wave or EEG sample is greater than some multiple of the standard deviation, preferably greater than about 3 times and more preferably greater than about 5 times, then that EEG sample is marked as an artifact and is replaced by a value that is derived from the artifact-free segment of the data immediately before. The artifact-free segment of data is that portion of the sampling data preferably greater than about 0.1 seconds before and also preferably less than about 0.6 before the artifact in sampling time.

This brain wave or EEG sample data is then preferably broken into consecutive sampling moments or time segments. These sampling moments or time segments are preferably 2 seconds in duration allowing for example 400 sampling points if the brain wave or EEG signal sampling rate was 200 samples per second. Each consecutive time segment is then transformed into a frequency domain representation (also known as power spectrum or frequency power spectrum) using techniques known to those skilled in the art. One technique, which is preferred, is to use a standard Fast Fourier Transform method (FFT). The FFT coefficients obtained are then squared and scaled to obtain the power spectrum plot (i.e., the power of brain wave or EEG signal at each frequency level). In this embodiment since the segment duration is for 2 seconds, the frequency resolution will be 0.5 Hz, and power values can be obtained for frequency bins of 0.5, 1, 1.5, 2, 2.5, ..., 50 Hz.

The power spectrum of each time segment is used to determine if the time segment contains movements and other types of artifacts. Some of the artifacts manifest themselves in abnormally large power values in all frequencies, particularly at very low frequencies <10 Hz, compared to the power spectrum of the entire study. Upon detection of such abnormally high power spectra, preferably the entire sampling segment (in this embodiment 2 seconds) is marked as contaminated by the artifacts and is replaced by an average power spectrum of the artifact-free segments.

Brain wave data that is monitored and analyzed according to the present invention is between about 0.1 to about 50 Hz.

Preferably, this data is between 0.1 to about 30 Hz, more preferably between about 0.1 to about 15 Hz, and most preferably between about 0.1 to about 13 Hz. Also in certain embodiments of the present invention brain waves are categorized as delta, theta, alpha and beta waves or components. Delta waves or components generally exhibit brain wave or EEG activity in the frequency range from about 1 Hz to about 4 Hz, theta waves or components generally in the frequency range from about 6 Hz to about 7.5 Hz, alpha waves or components generally in the frequency range from about 7.5 Hz to about 13 Hz, and beta waves or components generally in the frequency range from about 13 Hz to about 30 Hz. As those skilled in the art will appreciate, the boundaries between these components are somewhat arbitrary. Thus, the foregoing delineations are intended to be exemplary and not limiting. Furthermore, use of other components, whether now known or later discovered, are within the scope of the invention.

In one embodiment of the present invention, the frequency power spectrum or power spectrum is used to determine a number for each sampling moment or time segment, and an average number over a measurement time period, which may include numerous sampling moments or time segments is determined. This number is then compared with a predetermined threshold number which has been calculated (and in a sense calibrated) based on previous tests using this technique on individuals with no known sleeping disorders, and individuals with a range of known sleeping disorders. In a more specific embodiment, a number is obtained by using only the frequency power spectrum or power spectrum data at frequencies below about 13 Hz. In this embodiment, data at frequencies below about 13 Hz is subjected to some form of mathematical manipulation such as being input into an algorithm. As those skilled in the art will appreciate, the weighting of data from the various frequency power spectrums or power spectrum may vary as well as the number of power spectrum frequencies or power spectrum used in order to magnify the quantitative resolution of this method. In an even more specific embodiment of this sleep analysis method, a number is obtained at least in part based upon the sum of the power in the 0.5-7.5 Hz frequency (and even more preferably in the 4-7.5 Hz frequency) bands divided by the sum of the power in the 7.5-13 Hz frequency bands (and more preferably in the 7.5-9.5 Hz frequency bands) to determine a ratio or an average number over a given measurement time period or period of time. This number is then compared with a predetermined threshold number which has been calculated (and in a sense calibrated) based on previous tests using this even more specific technique on individuals with no known sleeping disorders, and individuals with a range of known sleeping disorders.

In another embodiment of the present invention, the frequency power spectrum or power spectrum is used to determine a profile of the subjects a sampling data over a period of time or measurement time period. The period of time or measurement time period for the profile may either be the entire testing period, some portion thereof, which may include numerous sampling moments or time segments. This profile is then compared with a predetermined threshold profile which has been determined based on previous tests using this technique on individuals with no known sleeping disorders, and individuals with a range of known sleeping disorders (or based on what is determined to be a typical profile for someone with no known sleeping disorder or for an individual with a specific sleeping disorder). In another more specific embodiment, a profile is obtained by using only the frequency power spectrum or power spectrum data at frequencies below about 13 Hz. In this more specific embodiment, data at frequencies below about 13 Hz is subjected to some form of mathematical manipulation such as being input into an algorithm to form the profile. As those skilled in the art will appreciate, the weighting of data from the various power spectrum frequencies may vary as well as the number of power spectrum frequencies or power spectrum used. In an even more specific embodiment of this sleep analysis method, a profile is obtained over a period of time equal to all or part of the test that at least in part based upon the sum of the power in the 0.5-7.5 Hz frequency (and even more preferably in the 4-7.5 Hz frequency) bands divided by the sum of the power in the 7.5-13 Hz frequency bands to determine an average number over a given period of time or measurement time period. This frequency power spectrum or power spectrum data is then plotted over time to create a profile for the subject over the measurement time period. This profile is then compared with a predetermined profile which has been determine based on previous tests using this same even more specific technique on individuals with no known sleeping disorders, and individuals with a range of known sleeping disorders (or based on what is determined to be a typical profile for someone with no known sleeping disorder or for an individual with a specific sleeping disorder).

In addition to the above techniques, many other methods of analyzing the data can be used to further enhance the resolution of the data between subjects and to eliminate any noise in the analyzed data. It is envisioned that the present invention includes those techniques and any other techniques know to those skilled in the art.

Figure 4:
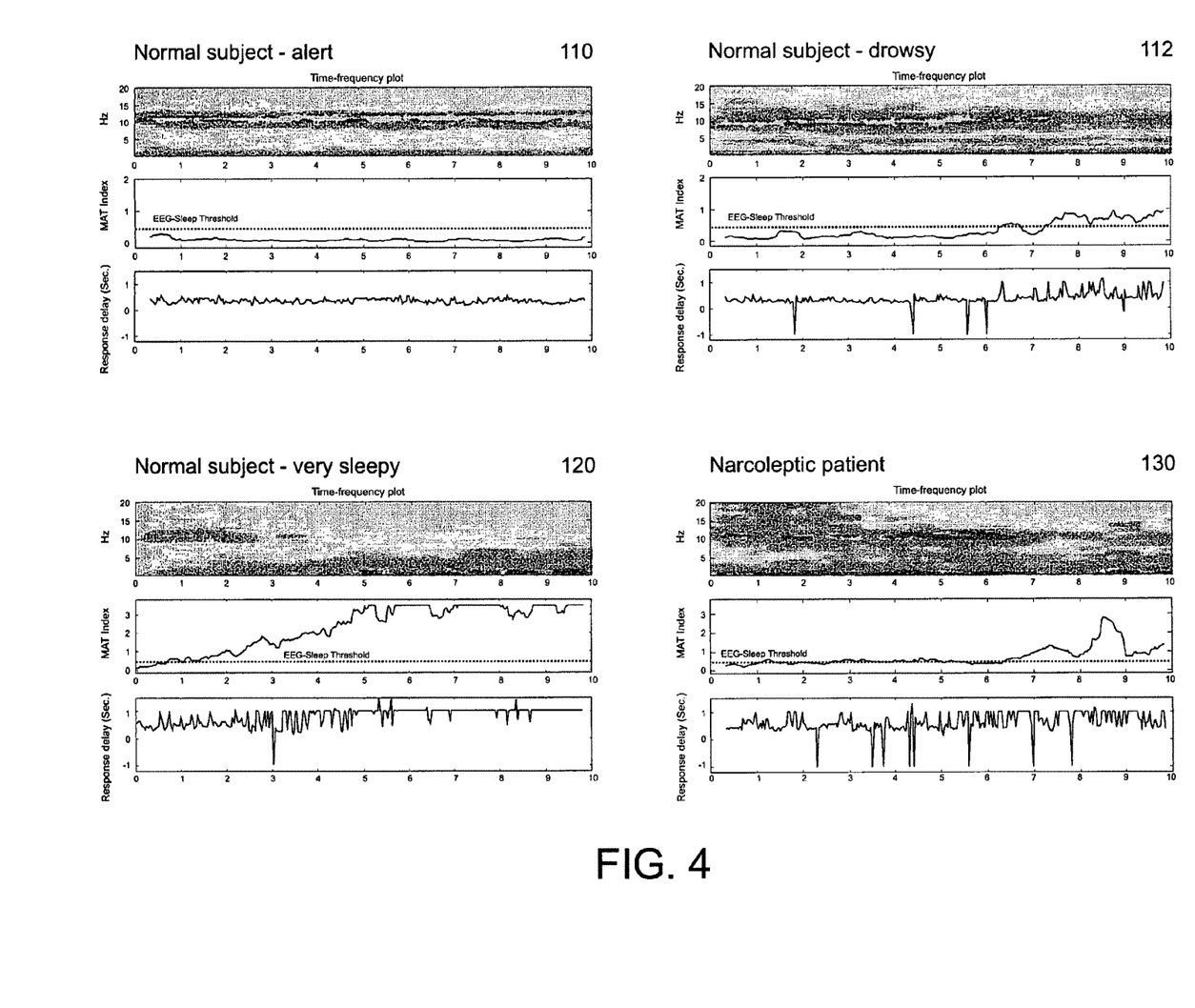
FIG. 4 are graphs showing data analyzed by one embodiment of the present invention for a variety of subjects.

FIG. 4 shows examples of the analyzed data obtained from the posterior EEG and push-button response of four different subjects performing a 10-minute MAT test. For each subject, from top to bottom, are the following three graphs: a Time-Frequency plot, a MAT-index, and a graph of the subject's response delay obtained from the push-button test. For the first graph, a Short-Term Fourier Transform Spectograph, lighter shades correspond to higher spectral powers. The second graph is related to the subject's level of alertness, and indicates a threshold level that separates the awake state from "EEG-based" sleep state. For the third graph, an error of omission (failing to respond to the target sound within one second) is assigned a value of 1, while an error of commission is assigned a value of −1.

Figure 5:
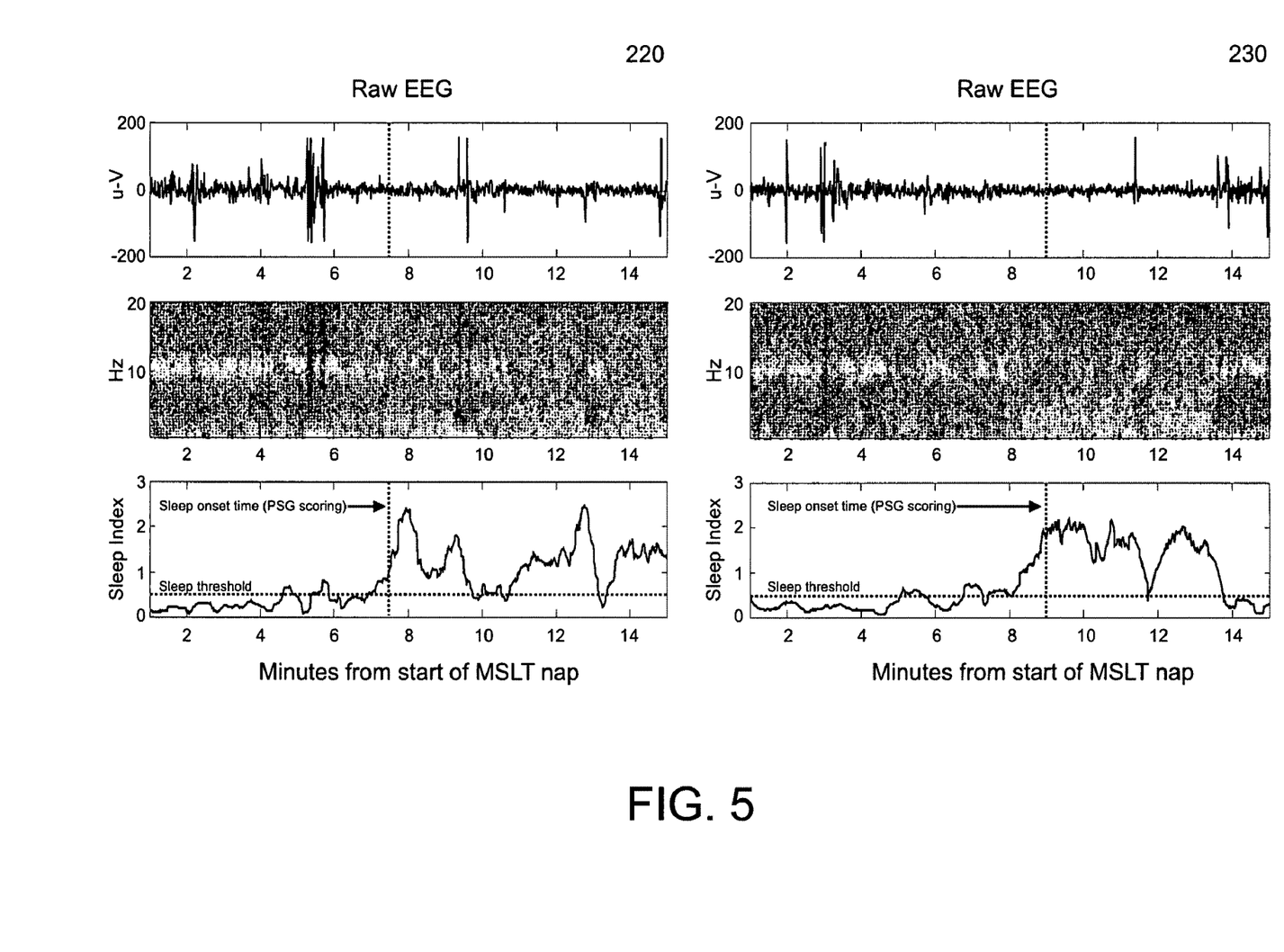
FIG. 5 are graphs of the analysis of the awake to sleep transition of a typical patient using one embodiment of the method of the present invention.

FIG. 5 shows the results of our analysis of the MSLT data from two naps of the For each nap, there is, from top to bottom, the raw EEG waveform (Occipital site), a Time-Frequency spectrogram where the lighter color indicates higher power levels, and our sleep index. Superimposed on the sleep index is the sleep threshold and sleep onset time that has been determined by the PGS technologist. For both naps, it can be noted that the sleep index reaches the threshold fairly quickly (~5 minutes) and bounces at that level for about 3 minutes before taking off into a sustained sleep.

Data can also be analyzed for excessive daytime sleepiness by another embodiment shown in U.S. Provisional Patent Application No. 60/691,750 which is herein incorporated by reference. This analysis utilizes a lightweight (3.4 Oz with 2 AAA batteries) and small (4.0"×2.2"×0.7") wireless EEG data acquisition unit that is based on Cleveland Medical Devices Inc. FDA-cleared Crystal™ 16 monitor. This hardware is capable of measuring up to 8 channels of EEG and transmitting them via a 902 to 928 MHz telemetry link to a commercial PC. One input channel of the unit has been modified to accept signals from a hand-held push-button to record the subject's cognitive response. The PC, located about 6 feet away from the subject, has a dual role of recording/displaying the EEG and push-button data (subject's reaction profile) as well as presenting a series of target and non-target auditory stimuli (less than 5 seconds apart presented in a random fashion) for a total test duration of 15 minutes. The subject, sitting comfortably with his/her eyes closed in a darkened and quiet room, is instructed to relax but to stay awake and press a push-button upon hearing the target stimuli while ignoring the non-target sound.

In the first stage of data processing, reaction time to each auditory stimulus is computed based on the time delay between the presentation of the sound and pressing of the push-button. As for the EEG, the time-varying spectrogram (Short-Term Fourier Transform) is computed using an analysis window that spans the time period between two consecutive stimuli. Thus, for each inter-stimulus interval, a quantity corresponding to the reaction time and a power spectrum of EEG is obtained. Each spectrum is further reduced to a single index value, referred to as Drowsiness-Sleepiness Index (DSI), using a general function show in equation (1).

In equation (1), Pnxx is the instantaneous power spectrum (computed using Short-Term Fourier Transform) at sample time n and $\theta_H$ depicts the high theta region (>5 Hz), $\alpha_L$ is the lower alpha band (<10 Hz), $\beta_L$ corresponds to lower beta (<16 Hz) and $\delta_H$ corresponds to higher delta region (>2 Hz) of the spectrum.

The parameters m, p, l, and q attribute different weightings to the integral of power in the various frequency bands. They were computed based on an optimization procedure with a cost function constructed from the dynamic cross-correlation between the time profiles of DSI and reaction times. The optimization criteria was to maximize the cross-correlations for lags≦0 (corresponding to Phase lead of DSI with respect to reaction times). Note that increased sleepiness corresponds to an increase in the DSI value as shown below.

$$DSI(n) = f\left(\frac{\sum P_n xx(\theta_H)^m \cdot \sum P_n xx(\delta_H)^p}{\sum P_n xx(\alpha_L)^l \cdot \sum P_n xx(\beta_L)^q}\right) \quad (1)$$

Figure 6:
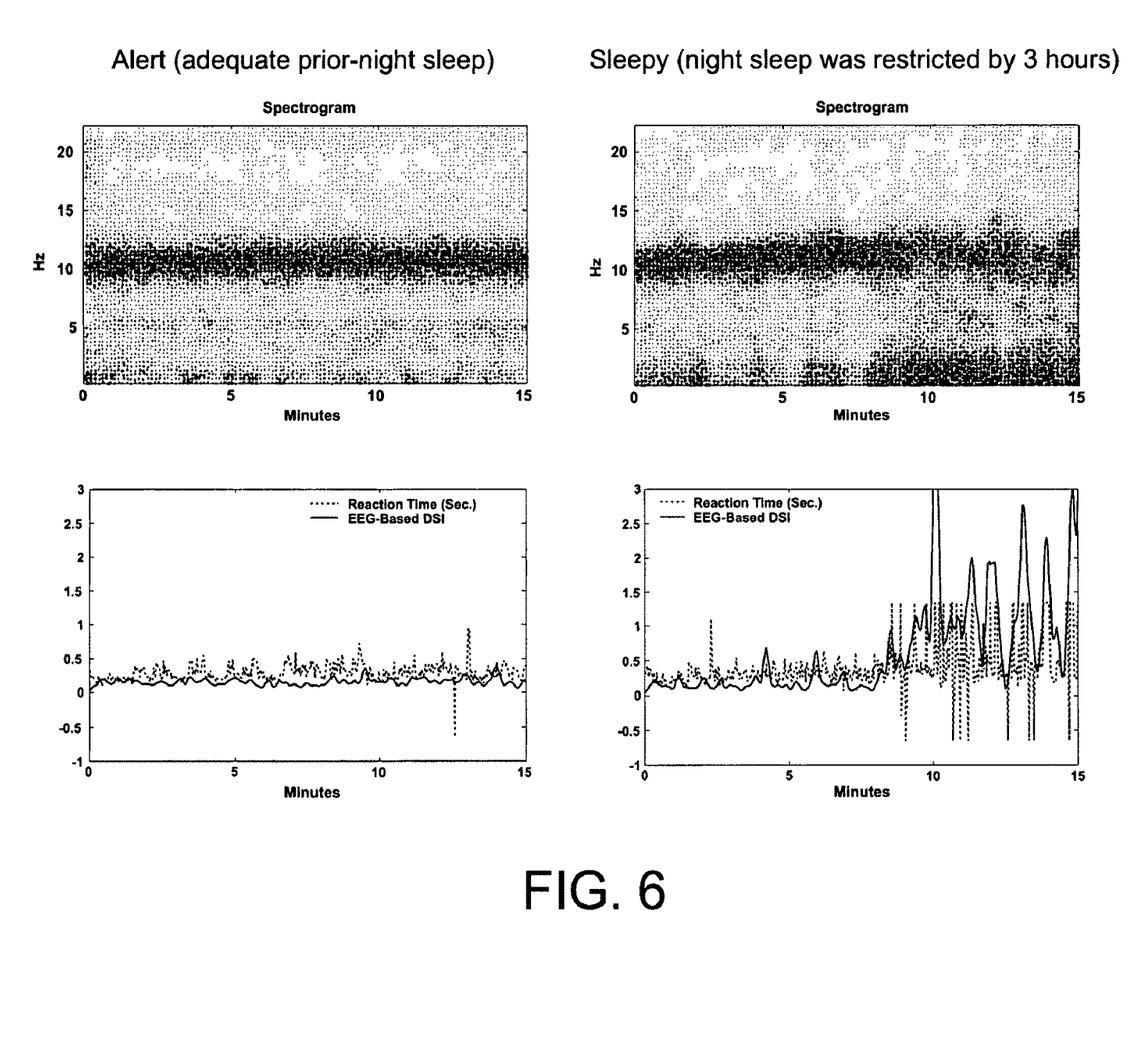
FIG. 6 are graphs depicting neurobehavioral indices computed for a subject under alert and sleepy conditions.

To illustrate the above analyses, FIG. 6 shows the processed neurobehavioral indices from a typical normal volunteer who has been tested under the alert (adequate prior night sleep, left columns) and sleepy (prior night sleep restriction, right columns) condition. The top row shows the spectrogram corresponding to the alert (top left) and sleepy (top right) conditions. For any given frequency band (horizontal slice), darker shading indicates higher power levels of the EEG. Thus in both spectrograms, there is initially high levels of power in the alpha band (~10 Hz). However, it is visually apparent that the spectrogram of the alert state shows a well-maintained high power α band throughout the 15-minute test. In contrast, the sleepy condition shows a deterioration of the α power several minutes into the test that coincides with an increase in the power of the lower frequencies (θ and δ). Please note that because of relative weakness of β power, the changes in that frequency band (as a result of sleepiness) are not apparent from this image.

The bottom left and right plots of FIG. 6 depict the reaction times (in seconds) to each auditory stimuli obtained from the push-button data from the alert (left) and sleepy (right) conditions. By convention, the omission errors (failure to respond to the sound) are assigned a maximum value corresponding to the average inter-stimulus period, while the commission errors (inappropriate response to the non-target tones) are assigned a negative value. The plots in FIG. 6 (bottom) also show the DSI (computed from equation 1) in solid lines superimposed on the reaction times (dashed lines).

Visual comparison of DSI with the reaction times, particularly for the sleepy-condition, reveals a good agreement between the two variables. Thus, in the alert state, DSI has a low value throughout the duration of the test (indicative of maximum alertness). In contrast, DSI of the sleepy-condition starts at a low value but shows occasional increased levels until ~7 minutes at which time it starts to increase steadily with large swings. Close examination of the reaction times reveal that the increase in DSI is closely matched by the prolongation of the reaction times. Furthermore, the graph shows a close relationship between the swings of DSI and those of the reaction times later in the test when the subject's drowsiness becomes very apparent.

Sleepiness Quantification Based on Neuro-Behavioral Indices

The results of FIG. 6 indicate that the EEG-based DSI appears to be a highly sensitive index of instantaneous level of drowsiness that is very closely matched with the behavioral (functional) drowsiness (indicated by the prolongation of reaction times and exaggerated number of omission and commission errors). In order to quantify the sleepiness level of the subject, an interval of the test (e.g., minutes 5 through 10) is specified and the average DSI, as well as the total number of prolonged reaction times (>0.6 seconds) are computed. The behavioral index, referred to as RT-Prolonged, is expressed as % of the total auditory stimuli for that time period. Also, a "hybrid" quantity that combines the average DSI with the RT-Prolonged has been utilized to produce an overall neuro-behavioral quantity to assess the degree of sleepiness.

Two sets of clinical experiments were performed to train the algorithms (particularly the parameters of the DSI index) and to validate the test in terms of its ability to discriminate alert from sleepy-condition. These tests were approved by the CleveMed's Institutional Review Board and informed consents were obtained from all of the subjects.

For the first set of experiments (training set), 10 normal volunteers were recruited to be tested under varying degrees of drowsiness/sleepiness (resulting from inadequate prior night(s) sleep). On the day of the test, 7 EEG electrodes were attached to multiple scalp locations (Frontal, Central, and Occipital regions of both hemispheres) using the standard gold cup electrodes. Then the subjects sat on a comfortable chair (recliner) for 15 minutes and were instructed to keep their eyes closed but try to stay awake and respond to the target tones as quickly as possible (press the pushbutton) while ignoring the other tones. With some subjects, the test was repeated after two hours to increase the size of the training set and to assess test's reliability and repeatability. The acquired data from these 10 subjects were used to fine-tune the algorithms and obtain the optimized numerical values for the DSI coefficients of (1).

The second set of experiments (validation data) involved a more formal experimental design as follows: After obtaining their informed consent, five normal volunteers participated in these studies (3 males and 2 females, age range: 23-43, no history of sleep or respiratory problems). Each subject was tested on two different days (between 9:00 AM and 11:30 AM) under the conditions of (1) adequate prior-night sleep and (2) prior night sleep restriction by 3 hours (subjects were instructed to stay awake for ~3 hours past their normal bedtime and wake up in the morning at their regular times.) These set of data were processed according to the neuro-behavioral algorithms described previously to assess the degree of correlation between the EEG-based and behavioral indices particularly around the time of transition from alertness to a state of severe drowsiness. In some sleep-restricted subjects, the pressure to fall asleep during the test was such that they actually entered stages 1 and 2 of sleep for prolonged periods of time (tens of seconds to several minutes). This enabled examination of the DSI algorithm in terms of its ability to track the transition from wakefulness to sleep. The results provided below are from the validation set and covers the analysis of the tests under the two conditions from each subject.

FIG. 6 has already shown the neurobehavioral indices computed for the same subject under the two conditions (alert, and sleepy). The data of FIG. 6 was typical in that unlike the alert-condition, none of the sleepy subjects could maintain their alertness throughout the entire 15-minute session. Thus after only a few (~5-7) minutes, the sleep-restricted subjects started to have prolonged reaction times leading to numerous omission errors (which sometimes became consecutive indicating the subject had fallen asleep). The EEG-based DSI also showed increased values around the time that the reaction times were prolonged.

Figure 7:
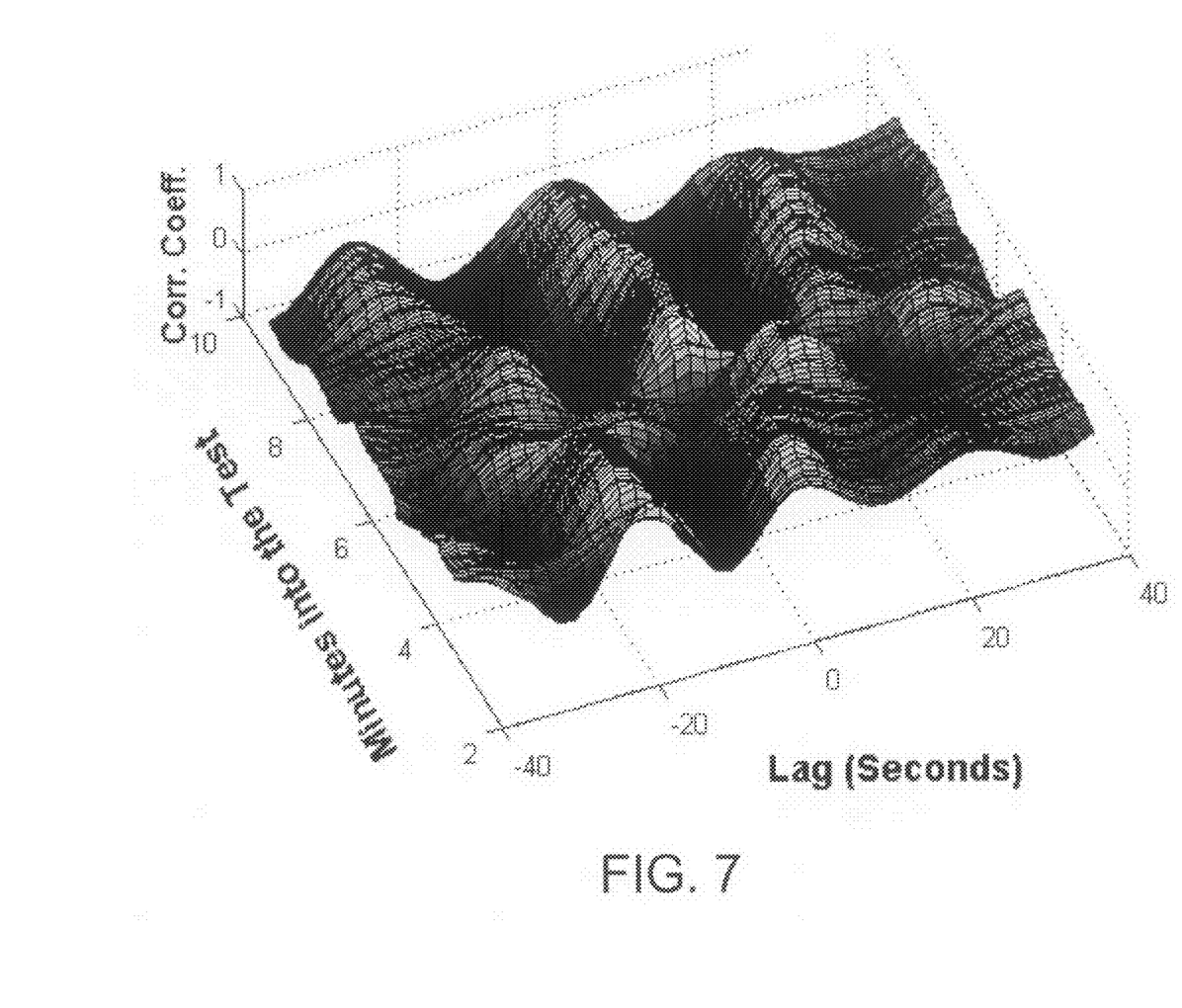
FIG. 7 is a graph showing correlation between behavioral and EEG-based indices.

To assess the agreement between the two indices, DSI was cross-correlated with the reaction times (and normalized by their respective auto-covariance) using a sliding analysis window. Both DSI and reaction time were band-pass filtered in order to reduce the effect of the DC (and very long trends) as well as the high frequency random noise. This is done to keep the analysis window short in order to obtain an acceptable time resolution for the time-varying cross-correlations. FIG. 7 shows the result of such cross-correlation analysis on the DSI and reaction time data of FIG. 1 (right column; sleep-restricted condition) around the time that the subject started to show signs of drowsiness. Please note that by convention, the peaks at negative lags correspond to a phase lead of DSI (i.e., variation in the DSI precede those in the reaction times).

FIG. 7 clearly demonstrates good correlation between the behavioral and EEG-based indices at and around lag zero. It is particularly interesting to note that DSI initially leads the reaction time variations by about 15 seconds. However, ~7 minutes into the test, when the first signs of omission errors occur (shown in FIG. 1), the peak correlation occurs around lag zero, indicating that the two indices had become synchronized. This result suggests that it may be possible to utilize DSI to anticipate degradation in the behavioral response which can lead to prolonged lapses of alertness.

Figure 8:
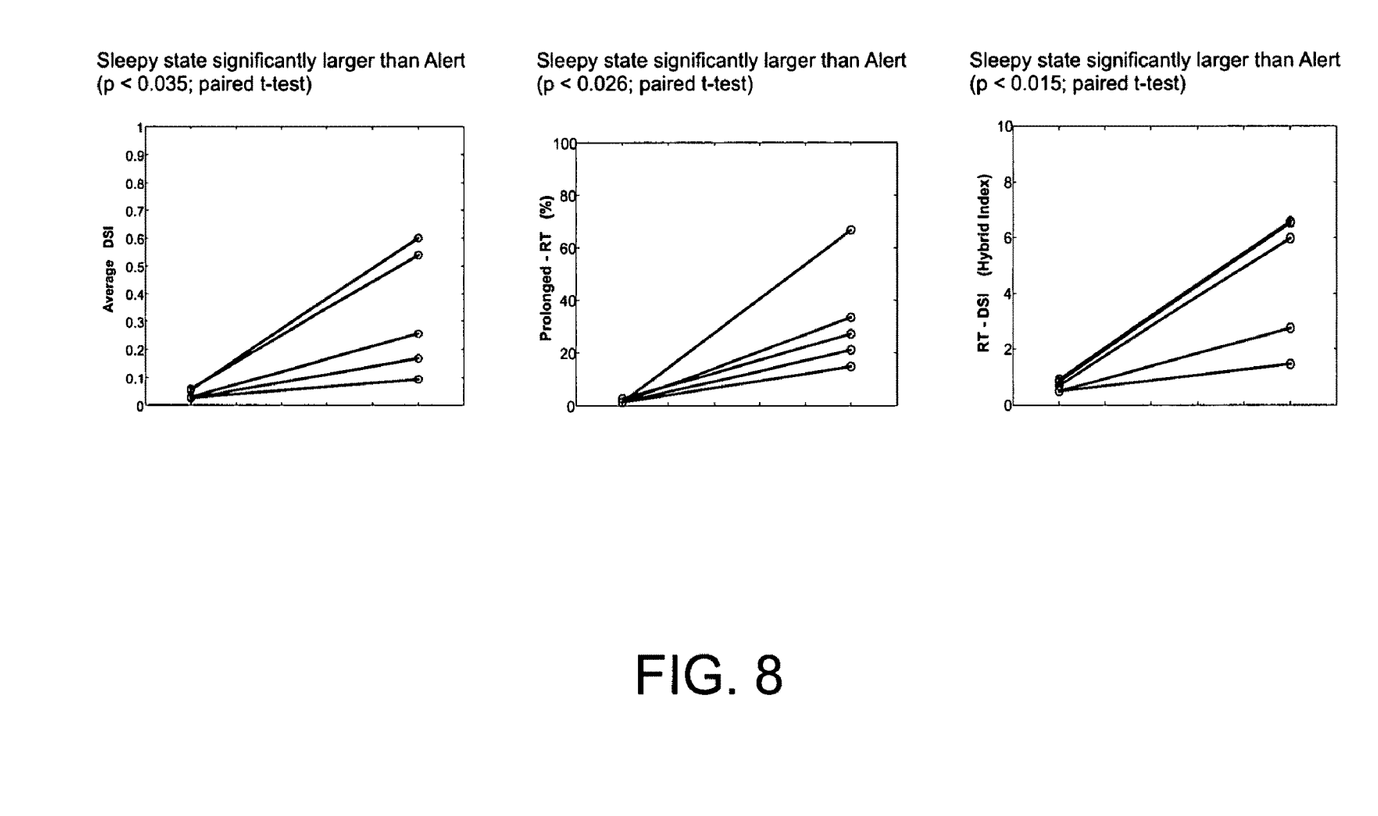
FIG. 8 are graphs showing capability of various embodiments of the present invention to discriminate alert from sleepy-conditions.

FIG. 8 shows the capability of the test to discriminate alert from sleepy-conditions in all of the 5 normal volunteers. Recall that sleepiness is quantified by three types of quantities: average DSI over a specified interval of the test (minutes 5-10), % of prolonged reaction times in that time period (referred to as RT-Prolonged index), and a hybrid index that combines these two neuro-behavioral indices (which is referred to as RT-DSI).

The left, middle, and right graphs of FIG. 8 show the average DSI, RT-Prolonged, and RT-DSI for the two conditions in all 5 subjects, respectively. In every subject, all three quantities could separate the two conditions by demonstrating higher values for the sleepy subjects compared with their alert states. Furthermore, paired t-test comparison between the two conditions shows statistical significance for all the three quantities with RT-DSI achieving a lower p value (p<0.015) compared with the others. This suggests that incorporating both EEG and behavioral data might increase the sensitivity of the method for detection/quantification of sleepiness. Finally, these results show that the effect of sleep restriction is highly pronounced in some subjects although the alert states of all subjects demonstrate very consistent quantities. This could suggest variable tolerance for sleep restriction in different individuals.

The neuro-behavioral test of the present invention shows improvement over current techniques for quantifying sleepiness and discriminating alertness from sleepy-condition using a relatively convenient and short-duration test protocol. The test utilizes a time-varying EEG-based Drowsiness-Sleepiness Index that demonstrates close agreement with behavioral response which can possibly provide early indication for an incipient lapse of alertness and vigilance. Further assessment of the technique is currently underway to quantify pathological sleepiness in various patient populations (sleep apnea, depression, etc.) before and after medication/therapy.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method of screening for sleep apnea comprising the steps of:
    a) measuring EEG signals of a subject using a sensor and analyzing EEG signals from the subject to a determine sleep onset time(s) over a measurement period;
    b) measuring respirations of the subject using a sensor and analyzing respirations of the subject to determine variability of the subject's respiration about the sleep onset time(s); and
    c) determining whether the subject has sleep apnea based in part on the variability of the subject's respirations about the sleep onset time(s).

2. The method in claim 1, wherein screening is performed to determine whether a subject has obstructive sleep apnea.

3. The method in claim 1, wherein the measurement period is less than two hours.

4. The method in claim 1, wherein the subject is screened in the subject's home or a doctor's office.

5. The method in claim 1, wherein the subject's EEG signals and respirations are measured and/or collected using a wireless data collection device.

6. The method in claim 1, wherein the respirations are measured using a respiration belt.

7. A method of screening for sleep apnea comprising the steps of:
    a) measuring EEG signals of a subject using a sensor and analyzing EEG signals from the subject to a determine sleep onset time(s) over a measurement period;
    b) measuring respirations of the subject using a sensor and analyzing respirations of the subject to determine variability of the subject's respiration about the sleep onset time(s);
    c) detecting an increase in respiratory variability about the sleep onset time(s) based at least in part on the measured and analyzed respirations of the subject;
    d) determining whether the subject is likely to suffer from sleep apnea based at least in part on the increase in respiratory variability; and
    e) scheduling the subject for a full or partial polysomnograph if the subject is likely to suffer from sleep apnea.

8. The method in claim 7, wherein the respirations of the subject are analyzed for less than about 4 minutes before or after the sleep onset time(s) to determine the subject's respiratory variability with respect to the subject's normal breathing pattern.

9. The method in claim 7, wherein the respirations of the subject are analyzed for less than about 60 seconds before or after the sleep onset time(s) to determine the subject's respiratory variability with respect to the subject's normal breathing pattern.

10. The method in claim 8, wherein the measurement period is less than two hours.

11. The method in claim 9, wherein the measurement period is less than two hours.

12. The method in claim 8 wherein the measurement period is less than 60 minutes.

13. The method in claim 9, wherein the measurement period is less than 60 minutes.

14. A method of screening for sleep apnea comprising the steps of:
   a) using a sensor to measure EEG signals of a subject over a measurement time period of less than about 60 minutes;
   b) using a sensor to measure respirations of the subject over the measurement time period of less than about 60 minutes;
   c) using a processing unit to analyze EEG signals from the subject to determine a sleep onset time(s) from the measured EEG signal;
   d) analyzing with the processing unit a variability of the subject's respirations about the sleep onset time(s); and
   e) determining whether the subject is likely to suffer from a respiratory-related sleep disorder based at least in part on variability of the subject's respirations about the sleep onset time(s).

15. The method in claim 14, wherein screening is performed to determine whether a subject has obstructive sleep apnea.

16. The method in claim 14 wherein screening is performed to determine whether a subject has central sleep apnea.

17. The method in claim 14 wherein the subject is screened in the subject's home or doctor's office.

18. The method in claim 14 wherein the sensor used to measure EEG signals of a subject is a dry electrode.

19. The method in claim 14 wherein the sensor used to measure a subject's respirations is a respiratory belt.

20. The method in claim 14 wherein the respirations of the subject are analyzed for less than about 4 minutes before or after the sleep onset time(s) to determine the subject's respiratory variability with respect to the subject's normal breathing pattern.

* * * * *